Figure 1:
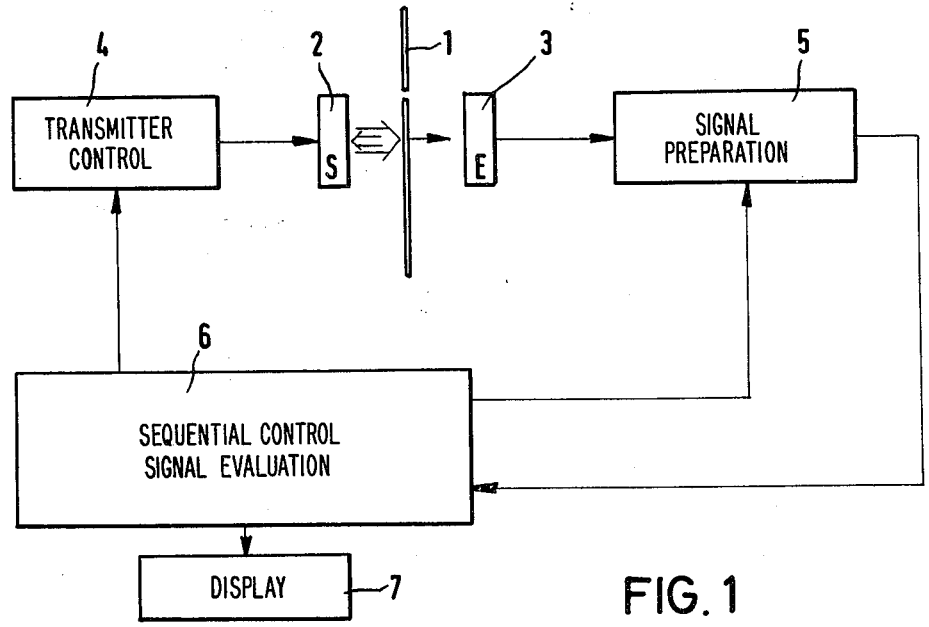

United States Patent [19]

Weilacher

[11] 4,446,735
[45] May 8, 1984

[54] METHOD OF TESTING THE WEIGHT PER UNIT AREA OF THIN MATERIAL

[75] Inventor: Karl H. Weilacher, Ampermoching, Fed. Rep. of Germany

[73] Assignee: GAO Gesellschaft fur Automation und Organisation mbH, Fed. Rep. of Germany

[21] Appl. No.: 323,315

[22] Filed: Nov. 20, 1981

[30] Foreign Application Priority Data

Dec. 23, 1980 [DE] Fed. Rep. of Germany ....... 3048710

[51] Int. Cl.³ .............................................. G01N 29/00
[52] U.S. Cl. ....................................... 73/597; 73/610; 73/159
[58] Field of Search ................ 209/590, 534; 271/263; 73/599, 613, 159, 160, 597, 610, 611, 612

[56] References Cited

U.S. PATENT DOCUMENTS

| | | | |
|---|---|---|---|
| 3,173,291 | 3/1965 | Simjian | 73/599 |
| 3,470,734 | 10/1969 | Agdur et al. | 73/159 |
| 3,848,460 | 11/1974 | Bantz et al. | 73/597 |
| 3,934,219 | 1/1976 | Monaghan | 73/599 X |
| 4,353,256 | 10/1982 | Moorey | 73/597 |
| 4,368,438 | 1/1983 | Stienstra | 73/159 |

FOREIGN PATENT DOCUMENTS 1548170 8/1969 Fed. Rep. of Germany .

Primary Examiner—Stephen A. Kreitman
Attorney, Agent, or Firm—Bacon & Thomas

[57] ABSTRACT

A method and a device for determining the weight per unit area and/or the thickness of thin material in sheets, for example banknotes, by aid of ultrasonic waves. The device comprises a single- or multi-channel transmitter-receiver arrangement in which the banknote passing through is exposed to a pulsating sound field. The sound is transmitted to the receiver via the banknote which is set vibrating by the sound. For the evaluation of the receiver signal a time interval dependent on the sound propagation time between the transmitter and the receiver is defined which begins when the primary sound arrives at the receiver and ends before reflected portions of the transmitted sound or portions of sound from adjacent transmitters arrive at the receiver. During the time interval the receiver signal which is free from noise signals is integrated. The integration value is a measurement of the density per unit area of the test material. A special integration method allows for the detection of two or more overlapping banknotes.

7 Claims, 4 Drawing Figures

METHOD OF TESTING THE WEIGHT PER UNIT AREA OF THIN MATERIAL

The invention relates to a method and/or a test device for the contactless determination of the weight per unit area and/or the thickness of thin material such as paper, foils and so on, whereby a transmitter exposes the material pulsatively to ultrasonic waves and receiver picks up the sound vibrations from the material.

The use of acoustic waves to determine the thickness of all kinds of materials has been known for some time.

The German patent application No. 15 48 170, for example, discloses a device for the contactless determination of the weight per unit area of paper by means of ultrasonic waves. The paper to be tested is exposed to a sound field by aid of a sound transmitter whereby the audio-frequency is set at 15,000 cycles per second. A receiver arranged opposite the transmitter or on the same side as the transmitter picks up the portion of sound coming from the paper. The receiving sound intensity is used as a measure of the weight per unit area of the paper.

When acoustic waves are coupled via air to a medium of considerably higher density than air, such as paper, the portion of sound reflected by the paper is very great, especially at higher frequencies. This means that the primary or direct sound of the transmitter penetrating the paper and reaching a receiver arranged on the other side of the paper, is overlapped due to multiple reflections between the transmitter and the paper or the paper and the receiver, by portions of sound of a similar order of magnitude as the primary sound. The phase relationship of these interferences varies relative to the phase relationship of the primary sound as a function of the position of the paper between the transmitter and the receiver. This leads to interferences with very variable amplitudes of the signal registered in the receiver.

The devices and/or methods disclosed in the German patent application have turned out not to yield sufficiently accurate or, in particular, reproduceable results. The sound isolation in the transmitter and/or receiver casing, as proposed in the German patent application, is no remedy as it has no influence on the reflection between the transmitter and the paper or the paper and the receiver, besides not being able to be carried out very effectively. If the isolation is put in the "path of rays" between the transmitter and the receiver when the transmitter and receiver are arranged opposite each other, as shown in an embodiment of the German patent application, the primary energy is weakened to the same degree. The unfavorable relation between the useful signal and reflection or noise signal remains unchanged.

The relation between the useful signal and the noise signal becomes even less favorable when, as also proposed in the German patent application, the receiver is arranged on the same side as the transmitter. In this case the portion of sound penetrating the paper, which is very weak anyway, is reflected towards the transmitter on a plate arranged behind the paper, and weakened a second time by the paper to the same degree. A reliable determination of the weight per unit area is practically ruled out for the above reasons in the case of this arrangement and the steps proposed in the German patent application.

The problem of the invention thus consists in proposing a method and/or a test device of the above-mentioned kind with which a very accurate and reproduceable determination of the weight per unit area of thin material is possible.

The problem is solved according to the invention by having the receiver be switched on after a delay as long as the sound propagation time between the transmitter and the receiver and being switched off before interferences caused by the system arrive at the receiver.

As essential feature of the solution according to the invention is thus that a time interval is defined for the evaluation of the receiver signal. The time interval begins dependent on the sound propagation time between the transmitter and the receiver when the primary sound arrives at the receiver, and ends before the first interferences (reflected portions of the transmitted sound or portions of sound from transmitters in the area) arrive at the receiver. Thus the test signal that is used for evaluation is free of interferences caused by the system. The elimination of these interferences also allows for the test signal to remain completely unaffected by considerable variations in the position of the paper.

Not only interferences may falsify the result of measurement, but also external noise. The influence of environmental noise is also reduced to an almost negligable level by the high acoustic frequency chosen for the method according to the invention, as well as by a special evaluation method discussed below in more detail.

Developments and further advantages of the invention can be found in the subclaims and in the following description of an embodiment.

Figure 4:
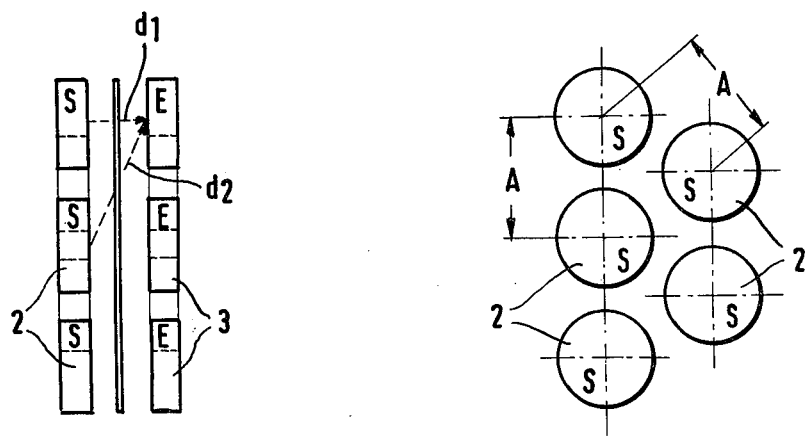
Figure 2:
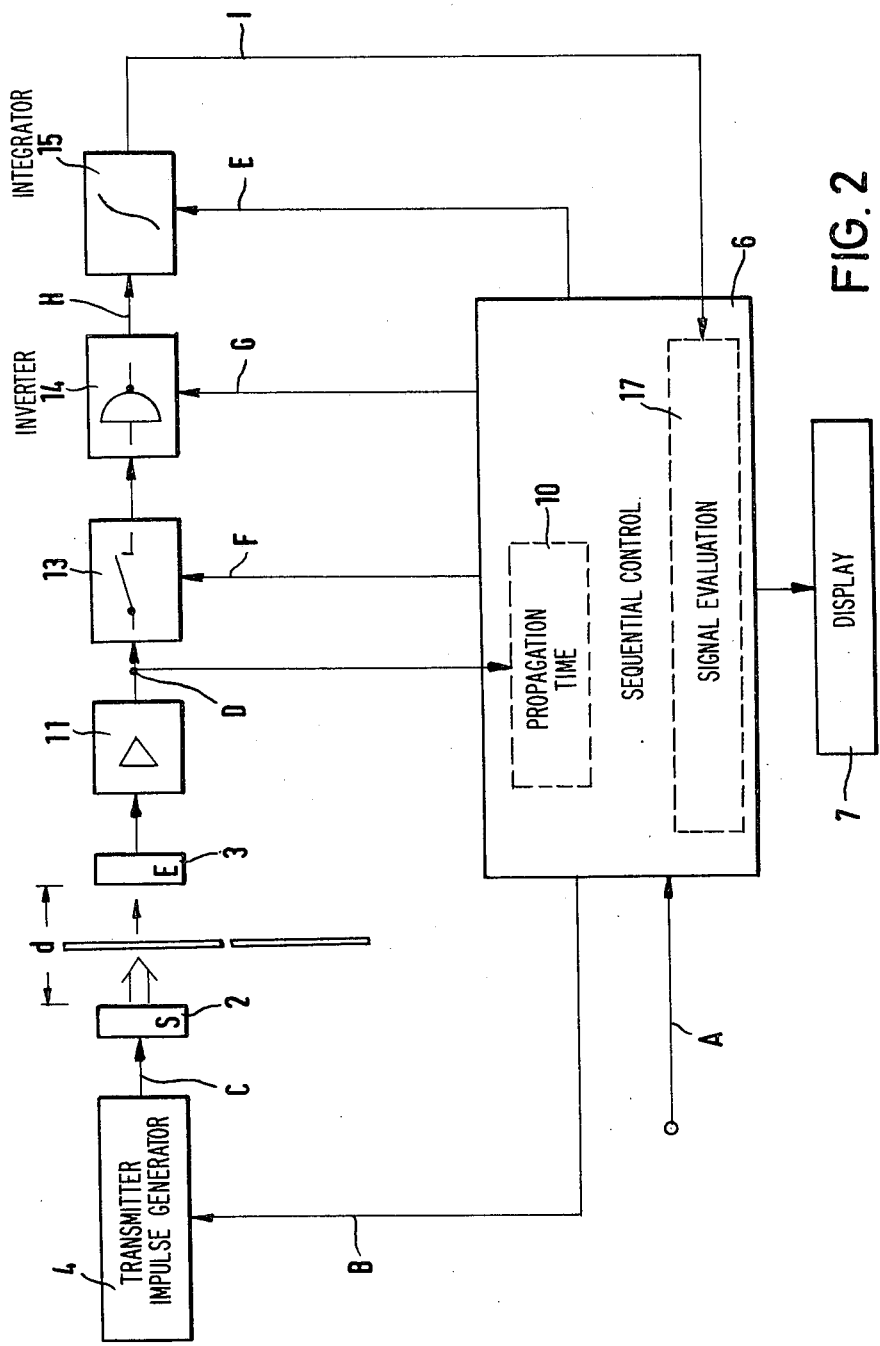
Figure 3:
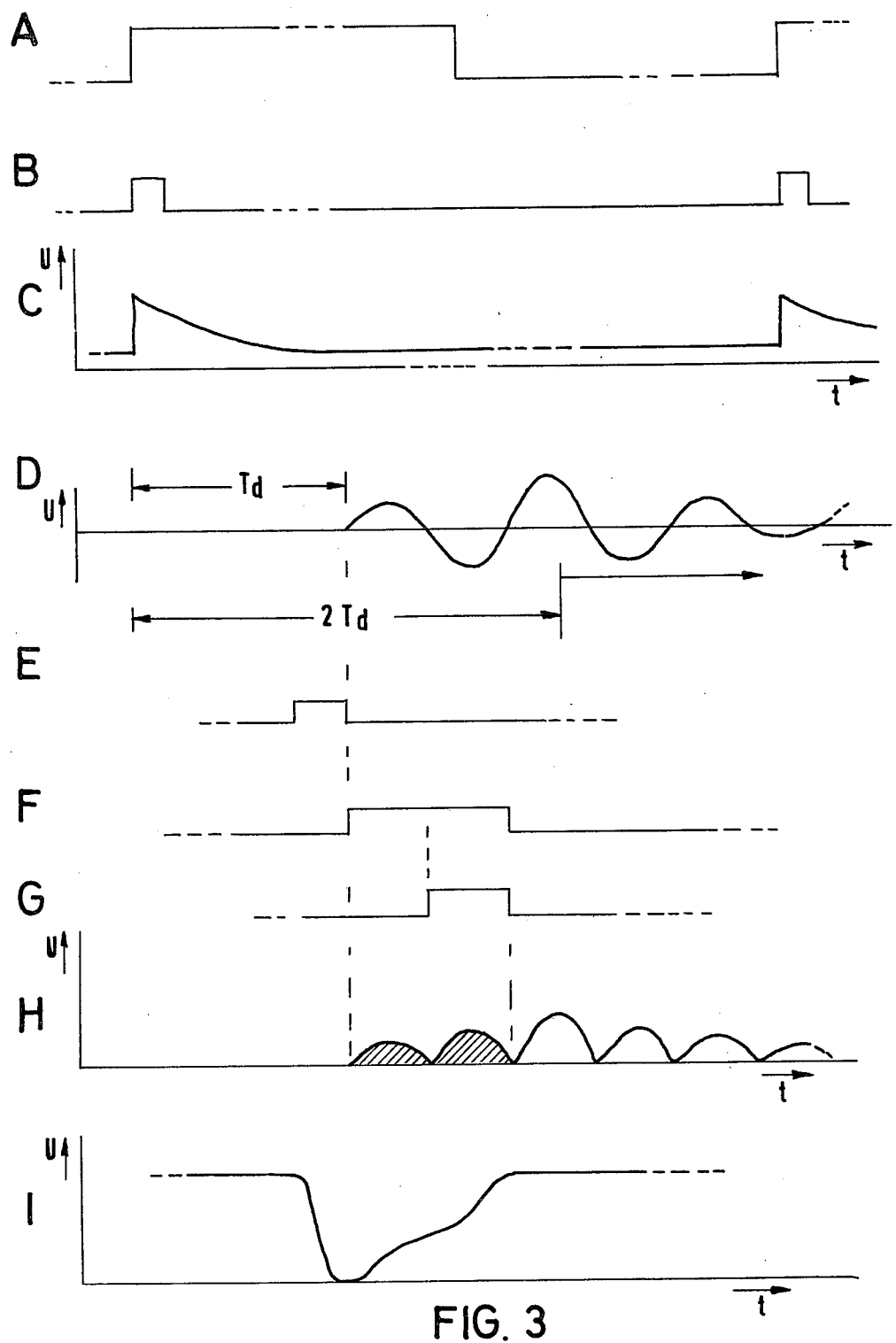

The figures show:

FIG. 1: the schematic representation of a test device to carry out the method according to the invention, FIG. 2: the electronic components of the test device in detail, FIG. 3: an impulse operation plan, and FIG. 4: a test device for scanning a large surface.

FIG. 1 shows by way of example the schematic representation of the test device for carrying out the method according to the invention.

The device can, for example, be inserted into banknote-sorting automata to determine the weight per unit area of banknotes. It is also possible for gum tape on banknotes or missing parts of banknotes to be recognized in the course of the determination of the weight per unit area in such a case. Another important task for banknote-sorting automata is the detection of double and multiple overlapped notes in order to ensure correct counting by the automata. The method according to the invention can be used advantageously especially for this function, as explained in more detail below.

In order to obtain high resolution for testing at very high transport speeds for the banknotes, the impulse recurrence frequency, which determines the number of measurements per unit of length on the banknote in the direction of transport, should be set accordingly high.

This frequency is limited, however, by the decay time of the transmitter vibration and the superimposed reflected portions of sound. The decay time of an acoustic vibration generated by an impulse is inversely proportional to the band width of the system generating the vibration.

The frequency of the transmitter vibration is important in addition to the impulse recurrence frequency.

The sound impulse that reaches the receiver is evaluated according to the invention with every transmitter impulse within the time interval defined above.

For reasons of a good signal/noise ratio the transmitter frequency in the case of great transmitting power should be so high, if possible, that at least one cycle of the receiver signal can be evaluated during the time interval.

Electret ultrasonic transducers have proved to be particularly well suited for the method according to the invention. The transducers have a high natural frequency with a wide-band frequency response and great transmitting power. An electret transducer stimulated by appropriate impulses generates a greatly dampened vibration at its natural frequency due to its band width.

As shown in FIG. 1, the banknote 1 goes through the transmit-receive arrangement 2, 3 in a central position. Appropriate single impulses are generated in the transmitter control 4 according to the sequential control 6 at regular intervals to stimulate the transmitter 2. The sound impulse released by the transmitter is reflected at the banknote for the most part. The non-reflected portion of the transmitter sound continues on the receiver side via the banknote paper that is set vibrating by the sound impulse.

The receiver 3 generates an analog signal which is processed in the signal preparation unit 5. In this unit the portion of sound is then integrated within a time interval predetermined by the sequential control 6. The final value of the integrator is evaluated in the signal evaluation contained in module 6, and then indicated. The integration value determined in the signal processing unit 5 is inversely proportional to the density by surface of the paper, which can be indicated, for example, directly in the corresponding units (g/m$^2$) after proper calibration in the indicator 7.

The determination and formation of the integration interval, along with further features essential to the invention, are described on the basis of FIGS. 2 and 3.

The beginning of the time interval for evaluating the receiver sound is determined by the sound propagation time between the transmitter 2 and the receiver 3.

The sound propagation time is measured in a component 10 of the sequential control 6 whenever there is no paper between the transmitter 2 and the receiver 3. The component 10 registers a very overriding signal at the output of the amplifier 11 in this case. The propagation time is then measured by a time measurement between the next impulse that arrives at the transmitter 2 via the impulse generator 4 and the corresponding impulse that appears at the receiver after a delay. In banknote-sorting automata the measurement of the propagation time can be carried out in the space between any two banknotes. The determination of the propagation time makes it superfluous to adjust the distance "d" between the transmitter and the receiver mechanically and exactly.

The continual determination of the propagation time also has the advantage that changes in propagation time due to temperature variations in the air between the transmitter and the receiver are automatically taken into account and thus do not influence the measurement result. The delay with which the integration of the receiver signal begins after a transmitter impulse, is set in the sequential control 6 dependent on the propagation time that has just been determined.

The device is controlled by a clock "A" fed to the sequential control (see also FIG. 3). This clock can be synchronized with the movement of the banknote. The signal "B" is generated in the sequential control dependent on the clock "A". This signal arrives at the transmitter impulse generator 4 which generates the voltage impulses suitable for the ultrasonic transducers (signal "C").

The steep leading edge of the impulses take care of the stimulation at the natural frequency of the transmitter. The transmitter impulse appears at the receiver after the propagation time $T_d$. The receiver signal amplified in module 11 is shown as signal "D" in FIG. 3. Due to the previous measurement of the propagation time, the gate signal "F" now can be set exactly when the sound signal appears at the receiver. The signal is led to switch 13 which then triggers integration.

When the banknote is directed midway between the transmitter and the receiver, the first reflected portion of sound (transmitter-banknote-transmitter-receiver) appears after the propagation time 2 $T_d$, since the path is twice as long. The integration is broken off according to the method of the invention before the first reflected portion of sound appears after the propagation time 2 $T_d$.

In the embodiment shown the end of the integration gate (signal "F") is set in such a way that exactly one period of the receiver signal is detected. In order to compensate variations in the position of the banknote, the distance "d" between the transmitter and the receiver is set as a function of the natural frequency in such a way that the reflected interferences only appear when integration is over after a safety interval compensating these variations. The integration of an entire period is a special case and is selected in the embodiment in the interests of clarity. Other forms are also possible.

After the integrator 15 is reset with the signal "E", the receiver signal is at first integrated positively. When the integration period is half over, which normally corresponds to half a period of the receiver signal under the conditions selected, the signal is inverted. For this purpose the signal "G" is fed to an inverter 14 so that the integrator adds up the inverted signal (signal "H") in the second half of integration.

This type of integration has, on the one hand, the advantage of filtering out disturbing noise. On the other hand, phase displacements of the signal are taken into account during integration. In the case of overlapped banknotes, then the banknotes are very close together, the phase of the receiver signal has proved to be displaced whereas the amplitude of the signal changes only very slightly relative to the testing of the single note. In this special case the integrator arrives at a lower final value due to the inversion of the signal in the center of the integration gate, in spite of the almost unchanged input amplitude, so that even in this case clear information is possible.

The evaluation of only one period of the receiver signal is very advantageous, in particular for the detection of overlapped banknotes.

The frequency response of the evaluation unit is comparable to that of a lock-in amplifier (band-pass response). External interfering noise therefore only plays a part in the range of natural frequency.

The final value of the integrator signal (signal "I") is fed to the evaluation unit 17 contained in the sequential control 6 and not specified here in more detail. It can be given as an absolute value, e.g. converted to g/m$^2$, or in the form of yes/no information after comparison with predetermined standard values, e.g. to indicate overlapped notes according to the testing function of the device.

FIG. 4 shows an embodiment of the device according to the invention suitable for scanning large areas of, for example, banknotes. Due to the special evaluation method discussed above it is possible to arrange the various transmitter-receiver pairs 2, 3 beside each other in a small space covering the area without the signals of the various transmitter-receiver arrangements disturbing each other.

The minimal distance "A" between the various transmitters depends on the distance "d" between the various transmitter-receiver arrangements. "A" is chosen to be so large that the sound of an adjacent transmitter only arrives at the corresponding receiver after the integration gate. The propagation time difference in the sound $(d_2-d_1)/C$ ($C \triangleq$ sonic speed) must therefore be larger than the length of the integration gate.

In the embodiment mentioned the method according to the invention was described in connection with the testing of banknotes in banknote-sorting automata.

The invention can be used with the same success to test the weight per unit area of paper or foil webs or similar thin materials.

What is claimed is:

1. A method for the contactless determination of the weight per unit area and/or the thickness of thin material such as paper, foils and the like, whereby a transmitter exposes the material pulsatively to ultrasonic waves and a receiver picks up the sound vibrations from the material wherein the sound propagation time $T_d$ between said transmitter and said receiver is determined and the receiver is switched on after a delay as long as the sound propagation time $T_d$ and is switched off after the elapse of a time period no greater than double the sound propagation time $T_d$, before interferences caused by the system arrive at said receiver.

2. A method according to claim 1, wherein the time interval defined by the switch-on time and the switch-off time is chosen such that at least one cycle of the vibrations of the transmitter is measured.

3. A method according to claim 2, wherein for evaluating one cycle of the signal, the signal supplied to an integrator is inverted after half a period of said received vibration has elapsed.

4. A method according to claim 1, wherein a transmitter is used which produces strongly attenuated vibrations having a frequency which corresponds to the resonance frequency of the transmitter.

5. A method according to claim 1, wherein single banknotes pass between said transmitter and said receiver and said sound propagation time is measured in the space between two banknotes after each determination of thickness.

6. A method according to claim 1, wherein a plurality ofi transmitter/receiver units is provided for scanning large surfaces of said material and the distances between the transmitter and the receiver of each of said units is such that transmitted sound of a unit reaches the receiver of an adjacent unit after the elapse of the time interval which is defined by the switch-on time and the switch-off time.

7. A method according to claim 1, wherein electret transducers are provided as said transmitter and/or said receiver.

* * * * *